United States Patent [19]
Jokobovits et al.

[11] Patent Number: 5,998,209
[45] Date of Patent: Dec. 7, 1999

[54] GENERATION OF LARGE GENOMIC DNA DELETIONS

[75] Inventors: Aya Jokobovits, Menlo Park, Calif.; Hirohisa Tsuda, Kanagawa, Japan

[73] Assignee: Abgenix, Inc., Fremont, Calif.

[21] Appl. No.: 08/808,139

[22] Filed: Apr. 16, 1997

Related U.S. Application Data

[63] Continuation of application No. 08/426,555, Apr. 21, 1995, abandoned.
[51] Int. Cl.$^6$ .............................. C12N 15/00; C12N 5/10
[52] U.S. Cl. ............................................ 435/463; 435/325
[58] Field of Search .................................... 435/463, 350, 435/351, 352, 363, 325

[56] References Cited

FOREIGN PATENT DOCUMENTS 9110741  7/1991  WIPO .

OTHER PUBLICATIONS

Zhang et al, Molecular and Cellular Biology vol. 14(4): pp. 2404–2410 (Apr. 1994).
Ramirez–Solis et al, Nature, vol. 378: pp. 720–724 (Dec. 14, 1995).

*Primary Examiner*—Terry McKelvey
*Attorney, Agent, or Firm*—Bret Field; Bozicevic, Field & Francis LLP

[57] ABSTRACT

The method of the invention provides the use of a replacement-type targeting construct to delete large fragments of genomic DNA by gene targeting. The replacement targeting construct, which may contain a selectable marker, is constructed to contain two regions of sequences which are homologous to the 5' and 3' flanking sequences of the targeted locus. After transfection of the targeting construct into the desired cell line, gene targeted-mediated deletions are identified by selection and further characterized. The invention is useful in any situation where one would want to create a large genomic deletion. Examples of suitable loci include MHC Class I and II antigens and immunoglobulin genes, including, for example, variable and constant region of kappa, lambda, or heavy chains.

18 Claims, 5 Drawing Sheets

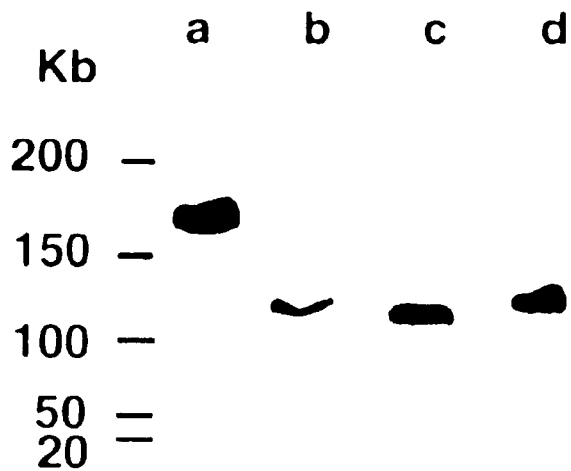
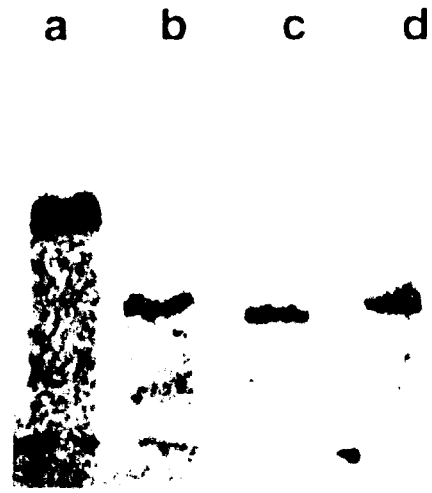
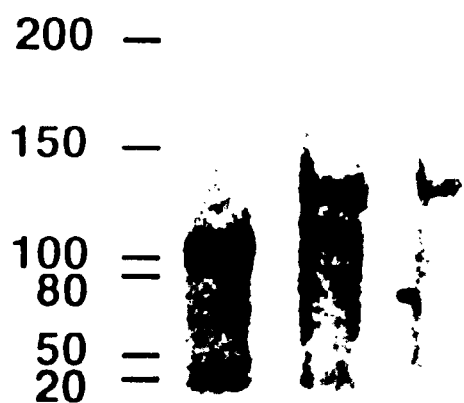
FIG. 3A   FIG. 3B   FIG. 3C   FIG. 3D

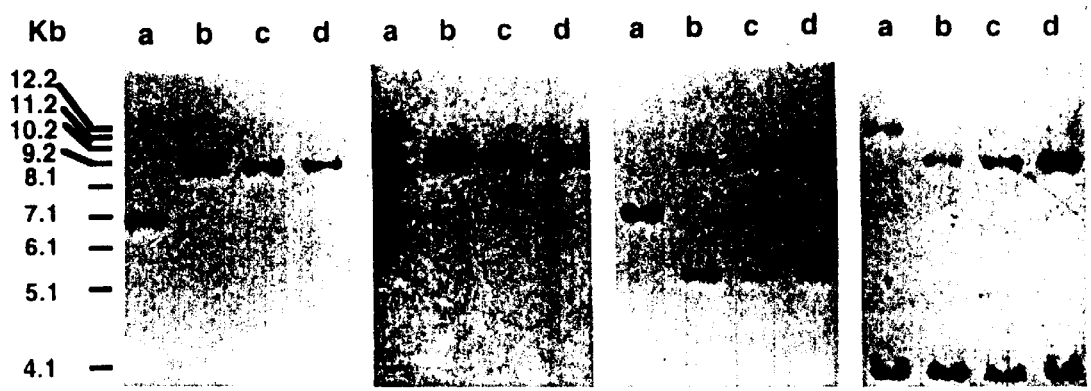

GENERATION OF LARGE GENOMIC DNA DELETIONS

This is a continuation of application Ser. No. 08/426,555, fled Apr. 21, 1995, now abandoned.

TECHNICAL FIELD

The field of the subject invention is the genomic modification of mammalian genes by generating large genomic DNA deletions using gene targeting with replacement-type targeting constructs.

BACKGROUND AND RELEVANT LITERATURE

Gene targeting by means of homologous recombination between exogenous DNA and endogenous homologous chromosomal sequences has proven to be a great tool to create a designed mutation or correct a gene mutation in cultured mammalian cells in mice, including mouse embryonic stem (ES cells) and upon "injection of the targeted E cells", to transmit these mutations into the mouse germline (Smithies et al., Nature, 317:230–234, 1985; Thomas et al., Cell, 51:503–512, 1987; Koller et al., Proc. Natl. Acad, Sci. USA, 86:8927–8931, 1989; Kuhn et al., Science, 254:707–710, 1991; Thomas et al., Nature, 346:847–850, 1990; Schwartzberg et al., Science, 246:799–803, 1989; Doetschman et al., Nature, 330:576–578, 1987; Thomson et al., Cell, 5:313–321, 1989; Shesely et al., Proc. Natl. Acad. Sci. USA, 88:4294–4298, 1991). It is also well appreciated in the field that the ability to create large deletions by gene targeting would be extremely useful, especially with respect to large genes or complexed loci which contain gene clusters and/or multiple copies. In these genes, complete targeting usually requires sequential targeting using differential markers which necessitates longer passages of the ES cells, during which transmission capability to germline may be reduced. Also for primary mammalian cells longer passages may affect their propensity to differentiate. While good sized deletions of 15 kb have been achieved in the T-cell antigen receptor β-subunit locus (Mombaerts et al., Proc. Natl. Acad. Sci. USA, 88:3084–3087, 1991), there remains a significant need for a method by which even larger genomic deletions can be achieved.

SUMMARY OF THE INVENTION

The present invention provides a method for obtaining a mammalian cell with a deletion greater than 15 kb in a target locus which comprises modifying the genome of a cell containing the wild-type locus by introducing a targeting construct comprising two regions of sequences which are homologous to the 5' and 3' flanking sequences of the region to be deleted in said wild-type locus. The method may further comprise culturing the modified cells in a medium containing a selectable agent and recovering cells containing said deletion. The target locus in the method of the invention can be any locus, for example, but not limited to, the HPRT, MHC Class I and II or immunoglobulin locus. The mammalian cell of the invention can be either primary cells or transformed cell lines, and may include any cell type including for example, the islets of Langerhans, adrenal medulla cells, osteoblasts, osteoclasts, epithelial cells, endothelial cells, B and T-lymphocytes, neurons, glial cells, ganglion cells, retinal cells, embryonic stem (ES) cells, liver cells, bone marrow cells, keratinocytes and myoblast (muscle) cells.

More specifically, the invention also provides a method for preparing a mammalian cell, including an ES cell, which is deficient in hprt. The method comprises introducing into target cells containing a wild-type hprt locus, a targeting construct which comprises a modified DNA fragment, which corresponds to the genomic site at which the wild-type hprt locus is located, wherein the modified DNA fragment comprises a first sequence immediately downstream of the second exon of the hprt locus congruent with wild-type sequence 55 kb upstream of said first sequence in the native DNA containing wild-type hprt locus.

BRIEF DESCRIPTION OF THE DRAWINGS

FIGS. 2A–2B and 3A to 3D depict pulse field gel electrophoresis (PFGE) of hprt gene locus in E14.1, E14TG2a, pm4.2 and pm5x.1 cells, as described in Example 1, infra. FIGS. 2A and 2B provide schematic illustrations of SacII and BssHII restriction sites in the hprt gene locus in E14.1 and pm4.2ES cells. In FIGS. 3A to 3D, a=E14.1; b=E14TG2a; c=pm4.2 and d=pm5x.1 in each panel DNA was digested with SacII (FIGS. 3A, 3B) or BssHII (FIGS. 3C, 3D) and probed with 5' probe (FIGS. 3A or 3C) or 3' probe (FIGS. 3B or 3D).

FIGS. 5A to 5D provide the results of Southern blot analysis of hprt gene locus in E14.1 (column a) E14TG2a (column b); and targeted ES clones pm4.2 (column c) and pm5x.1 (columnd). DNA was digested with BamHI (FIGS. 5A and 5B) or with BamHI/ClaI (FIGS. 5C and 5D) and was probed with 5' probe (FIGS. 5A and 5C) or with 3' probe (FIGS. 5B and 5D).

DETAILED DESCRIPTION OF THE SPECIFIC EMBODIMENTS

Figure 1:
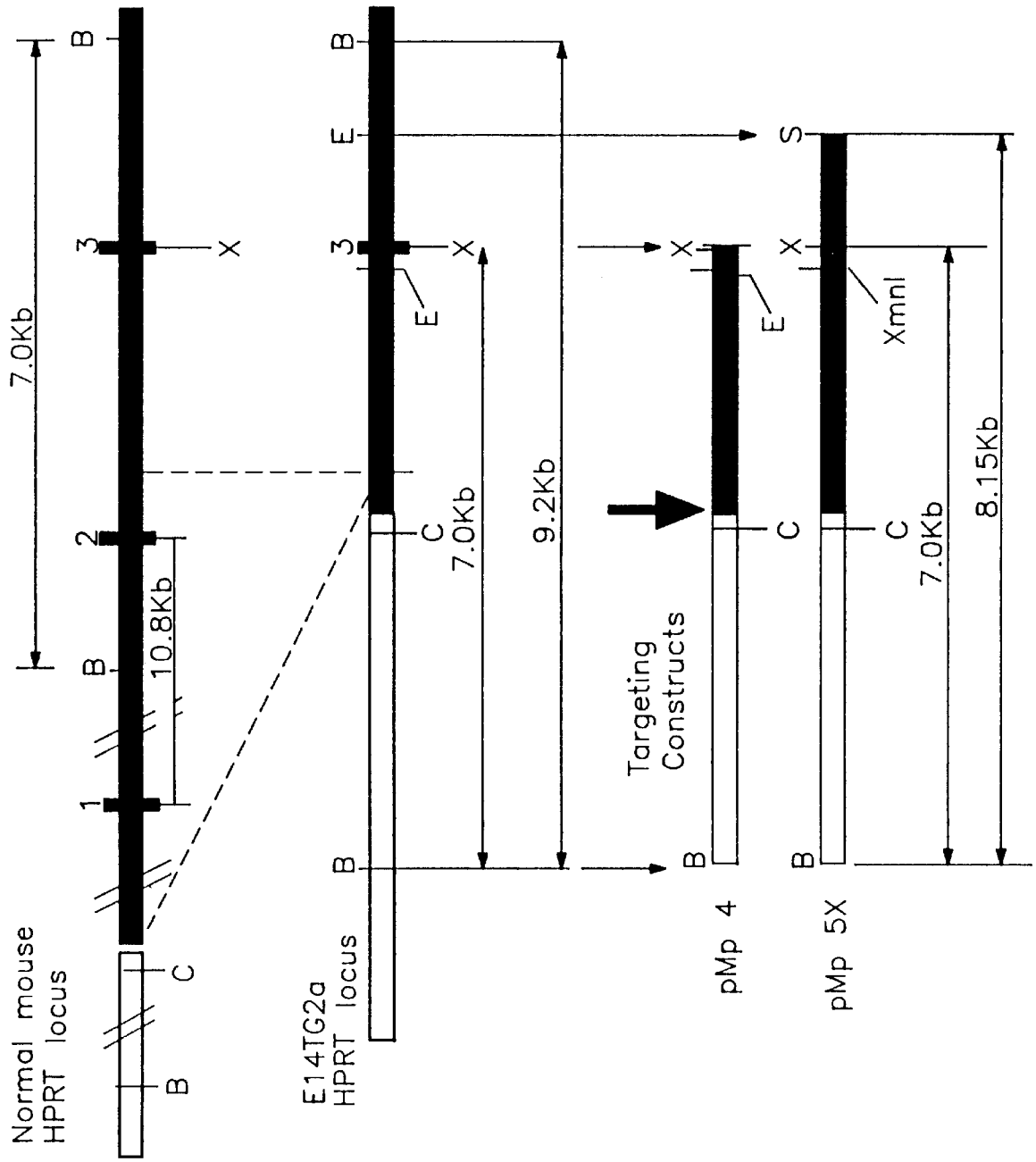
FIG. 1 depicts the hprt locus in normal mouse and mutant E14TG2a cells and targeting constructs used to delete 55 kb, as described in Example 1, infra (Restriction enzyme sites: B; BamHI, C; ClaI, E; EcoRI, X; XhoI, SS; SalI and XmnI).
Figure 2A:
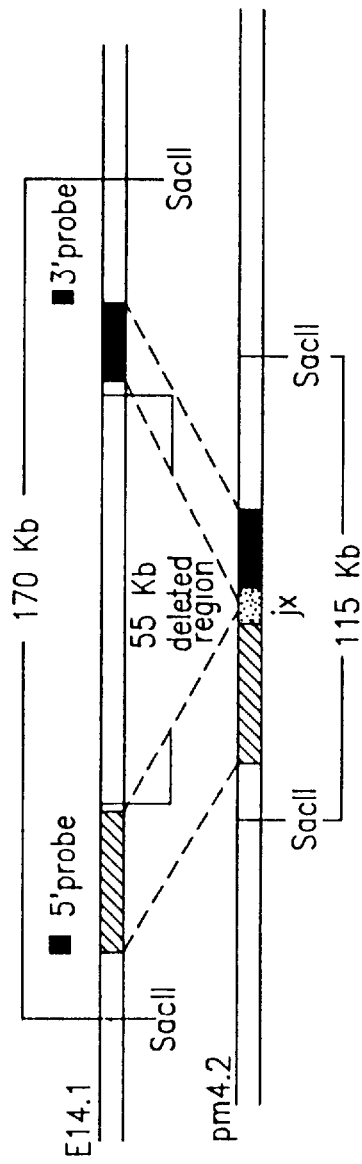
Figure 2B:
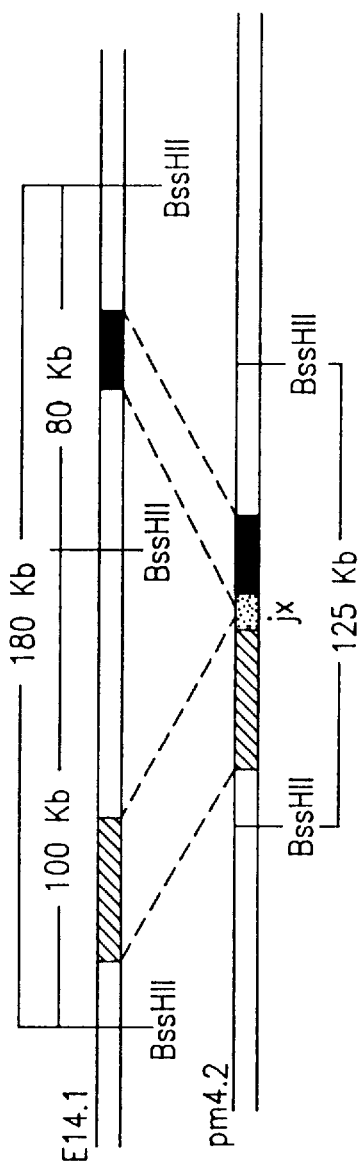
Figure 4:
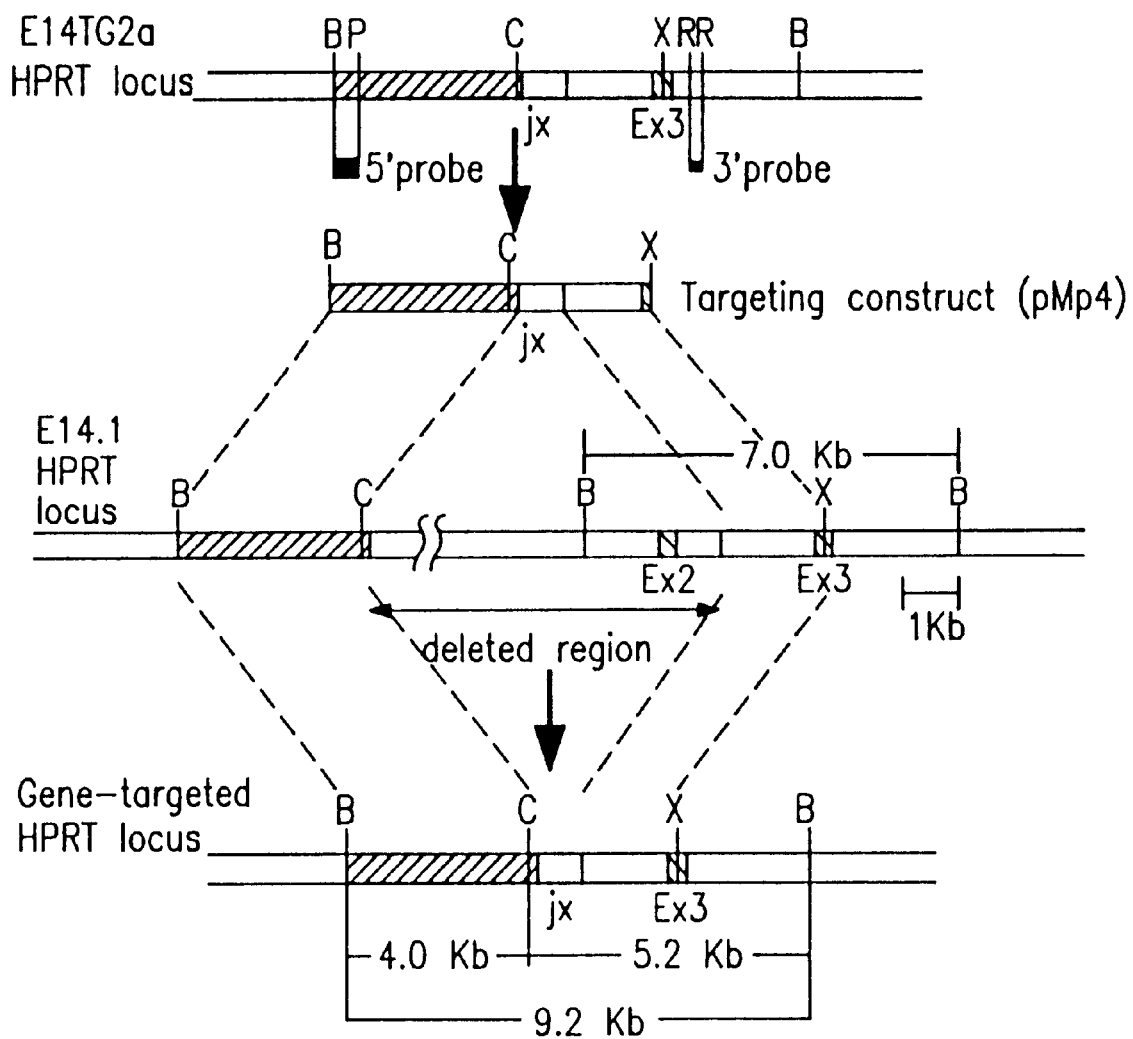
FIG. 4 depict inactivation of these mouse hprt locus by gene-targeted 55 kb deletion, using the targeting construct (pMp4), as described in Example 1, infra. The probes used for analysis (5' and 3' probe) and the structure of the hprt gene around targeted region in E14.1 cells, E14TG2a cells and targeted clones obtained: B; BamHI, C; ClaI, X; XhoI, R; RsaI, jx; junction and Ex; exon.

The method of the invention provides the use of a replacement-type targeting construct to delete large fragments of genomic DNA by gene targeting. The replacement targeting construct, which may contain a selectable marker, is constructed to contain two regions of sequences which are homologous to the 5' and 3' flanking sequences of the targeted locus. After transfection of the targeting construct into the desired cell line, gene targeted-mediated deletions may be identified by selection and further characterized by Southern blot analysis and pulsed field gel electrophoresis (PFGE).

It should be emphasized that the invention may be used for generating deletions in any locus in which one would want to create large genomic deletions for any purpose including, for example, research, therapeutics, and generation of cell lines or transgenic mammals. Examples of suitable loci include T-cell receptor, major histocompatibility complex (MHC) Class I and II antigens and immunoglobulin loci including, for example, genes encoding variable and constant regions of the kappa, lambda, or heavy chain loci. Additional examples of loci include low density lipoprotein (LDL), Apolipoprotein E, Apolipoprotein B, Factor VIII, Factor IX, CS transmembrane regulator, and the dystrophin gene. The cells and transgenic mammals which contain the large genomic deletions may be used to study gene structure and function or biochemical processes such as, for example, protein production or inhibition. In addition, the transgenic mammals may be used as a source of cells, organs, or tissues, or to provide model systems for human disease, such as for example, muscular dystrophy, immune system disorders, hypercholesterolemia, hemophilia, and cystic fibrosis.

The transgenic mammals may be any non-human mammal, particularly non-primate mammals, such as laboratory animals, particularly small laboratory animals, such as mice, rats, guinea pigs, etc., domestic animals, pets, etc. The transgenic mammals may be used experimentally to screen drugs or study biochemical pathways. The transgenic mammal, preferably a mouse, may also be used to produce xenogeneic, preferably human, or modified antibodies, as described in PCT applications, PCT/US91/00245 and PCT/US93/06926, herein incorporated in their entirety by reference. Large genomic deletions are created in the endogenous immunoglobulin loci in mouse embryonic stem cells, and in a separate step, the human heavy and light chain immunoglobulin gene complexes are introduced into the mouse germ line. This is accomplished by reconstructing the human heavy and light chain immunoglobulin genes in an appropriate eukaryotic or prokaryotic microorganism and introducing the resulting DNA fragments into the pronuclei of fertilized oocytes or embryonic stem cells, preferably from a mouse. Chimeric mice are generated which are derived in part from the modified embryonic stem cells and are capable of transmitting the genetic modifications through the germ line, Mating mouse strains containing human immunoglobulin loci to strains with strains in which the mouse immunoglobulin loci has been deleted generates mice which produce purely human antibodies.

Cells which may be subjected to gene targeting may be any mammalian cells of interest, and include both primary cells and transformed cell lines, which may find use in cell therapy, research, interaction with other cells in vitro or the like. Cells of particular interest include, but are not limited to, the islets of Langerhans, adrenal medulla cells, osteoblasts, osteoclasts, epithelial cells, endothelial cells, B and T-lymphocytes, neurons, glial cells, ganglion cells, retinal cells, embryonic stem (ES) cells, liver cells, bone marrow cells, keratinocytes and myoblast (muscle) cells. The cells may be obtained from any mammalian host, preferably human, and also including murine and other rodents, lagomorphs, porcine, feline, bovine, canine, etc.

The replacement targeting construct will comprise at least a portion of the endogenous gene(s) at the selected locus for the purpose of introducing a deletion into at least one, preferably both, copies of the endogenous gene(s), so as to prevent its expression. When the deletion is introduced into only one copy of the gene being inactivated, the cells having a single unmutated copy of the target gene are expanded and may be subjected to a second targeting step, where the deletion may be the same or different from the first deletion and may overlap at least a portion of the deletion originally introduced. In this second targeting step, a targeting construct with the same arms of homology, but containing a different mammalian selectable marker, for example the hygromycin resistance gene (hyg$^r$) may be used to produce a clone containing a homozygous deletion. The resulting transformants are screened by standard procedures such as the use of negative or positive selection markers, and the DNA of the cell may be further screened to ensure the absence of a wild-type target gene, by standard procedures such as Southern blotting. Alternatively when ES cells are targeted and are used to generate mice which are heterozygous for the deletion, homozygosity for the deletion may be achieved by cross breeding the heterozygous mice.

Another means by which homozygous deletions can be created in mammalian cells without the use of a second targeting step involves homogenotization of the gene targeting event, as described in PCT application, PCT/US93/00926, herein incorporated in its entirety by reference. In this method, the targeting construct is introduced into a cell in a first targeting step, to create the desired genomic deletion. The cells are then screened for gene-targeted recombinants, and the recombinants are exposed to elevated levels of the selection agent for the marker gene, in order to select for cells which have multiple copies of the selective agent by other than amplification. The cells are then analyzed for homozygosity at the target locus.

DNA vectors may be employed which provide for the desired introduction of the targeting construct into the cell. The constructs may be modified to include functional entities other than the deletion targeting construct which may find use in the preparation of the construct, amplification, transfection of the host cell, and integration of the construct into the host cell.

The replacement targeting construct may include a deletion at one site and an insertion at another site which includes a gene for a selectable marker. Of particular interest is a gene which provides a marker, e.g., antibiotic resistance such as neomycin resistance. The presence of the selectable marker gene inserted into the target gene establishes the integration of the target vector into the host genome. However, DNA analysis will be required in order to establish whether homologous or non-homologous recombination occurred. This can be determined by employing probes for the insert and then sequencing the 5' and 3' regions flanking the insert for the presence of DNA extending beyond the flanking regions of the construct or identifying the presence of a deletion, when such deletion is introduced.

Techniques which may be used to introduce the replacement targeting construct into the mammalian cells include calcium phosphate/DNA coprecipitates, microinjection of DNA into the nucleus, electroporation, bacterial protoplast fusion with intact cells, transfection, lipofection or the like. The DNA may be single or double stranded, linear or circular, relaxed or supercoiled DNA. For various techniques for transfecting mammalian cells, see Keown et al., *Methods in Enzymology* (1990) Vol. 185, pp. 527–537, incorporated by reference herein.

The genomic deletion will be greater than 15 kb and preferably, will be within the range of 50 kb to 3000 kb. The deletion will normally include at least a portion of the coding region including a portion of or one or more exons, a portion of or one or more introns, and may or may not include a portion of the flanking noncoding regions, particularly the 5'-non-coding region (transcriptional regulatory region). Thus, the homologous region may extend beyond the coding region into the 5'-noncoding region or alternatively into the 3'-non-coding region. The homologous sequence should include at least about 500 bp.

Upstream and/or downstream from the target gene construct may be a gene which provides for identification of whether a double crossover has occurred. For this purpose, the herpes simplex virus thymidine kinase gene may be employed, since the presence of the thymidine kinase gene may be detected by the use of nucleoside analogs, such as acyclovir or gancyclovir, for their cytotoxic effects on cells that contain a functional HSV-tk gene. The absence of sensitivity to these nucleoside analogs indicates the absence of the thymidine kinase gene and, therefore, where homologous recombination has occurred that a double crossover event has also occurred.

The targeting construct may further include a replication system which is functional in the mammalian host cell. For the most part, these replication systems will involve viral replication systems, such as Simian Virus 40, Epstein-Barr virus, papilloma virus, adenovirus and the like.

Where a selectable marker gene is involved, as an insert, and/or flanking gene, depending upon the nature of the gene, it may have the wild-type transcriptional regulatory regions, particularly the transcriptional initiation regulatory region, such as a promoter or enhancer, or a different transcriptional initiation region, . Whenever a gene is from a host where the transcriptional initiation region (promoter) is not recognized by the transcriptional machinery of the mammalian host cell, a different transcriptional initiation region (promoter) will be required. This region may be constitutive or inducible. A wide variety of transcriptional initiation regions have been isolated and used with different genes. Of particular interest are the promoter of metallothionein-I and II from a mammalian host, thymidine kinase, β-actin, immunoglobulin promoter, human cytomegalovirus promoter, SV40 promoter and polyoma virus promoter. In addition to the promoter, the wild type enhancer may be present or an enhancer from a different gene may be joined to the promoter region.

The targeting construct may further include a replication system for prokaryotes, particularly *E. coli,* which may be used in preparing the vector, cloning after each manipulation, analysis, such as restriction mapping or sequencing, expansion of the clone and isolation of the plasmid for further manipulation. When necessary, a different marker may be employed for detecting bacterial transformants.

Once the targeting construct has been prepared, it may be further manipulated by deletion or linearization of the bacterial sequences, where a short deletion, eg., 60 bp, may be provided in the homologous sequence. The small deletion will generally be near one or other end of the targeted structural gene. After such preparation, the construct is now ready to be introduced into the target cells. As already indicated, any convenient technique for introducing the DNA into the target cells may be employed. After introduction of the targeting construct, targeted cells may be selected by means of positive and/or negative markers, as previously indicated, such as neomycin resistance and acyclovir or gancyclovir resistance. Those cells which show the desired phenotype may then be further analyzed by restriction analysis, electrophoresis, Southern analysis, polymerase chain reaction (PCR) pulsed field gel electrophoresis (PFGE) or the like. By identifying fragments which show the presence of the deletion(s) at the target gene site, one can identify cells in which homologous recombination has occurred to inactivate one of the two copies of the target gene. In particular, PCR may be used with advantage in detecting cells in which gene targeting has occurred. Primers may be used which are complementary to a sequence within the construct and complementary to a sequence outside the construct and at the target locus. In this way, one can only obtain DNA duplexes having both of the primers present in the complementary chains if homologous recombination has occurred. By demonstrating the presence of the primer sequences or the expected size of PCR product sequence, the occurrence of homologous recombination is confirmed.

The second construct will differ from the first construct in not necessarily requiring a marker for selection, since the absence of the target gene product, eg., hprt, may be used as a marker. Thus, one may again use insertions, deletions or replacements for modifying and inactivating the target gene.

Another method for detecting cells in which the target gene has been deleted and which is especially useful when targeting genes which encode MHC Class I or II antigens, or immunoglobulin regions, involves the use of targeting constructs and an ELISA-based detection system, permitting the rapid detection of numerous independently targeted clones. In this method a site for homologous recombination is designed to create a recombinant fusion protein driven by a strong enhancer/promoter, for example the human CMV enhancer, fused to the domain of a protein containing an epitope, such as CD4. The epitope can be detected by a ligand to which it binds, for example an antibody, where the recombinant fusion protein is secreted by a correctly targeted cell and is then detected using an ELISA-based system employing antibodies that recognize the secreted fusion protein. In this method, the 5' end of the recombinant locus is derived from the targeting construct, while the 3' end of the locus is derived from the target gene. Because the entire 5' end is controlled experimentally, both the recombinant fusion protein's expression level and ultimate transport fate can be directed. Media is screened to detect the fusion protein in an ELISA which traps proteins containing a $\beta_2$-microglobulin epitope and detects proteins containing a CD4 epitope. This method may be used for other mammalian cell types, including ES cells. In addition to a CD4 epitope, other peptides that contain an epitope recognized by a ligand, such as an antibody that binds to the epitope, may be used in the fusion protein.

When embryonic stem cells, particularly ES cells from a murine host, have been targeted, it may be desirable to use such cells to generate transgenic animals. For such a procedure, following the introduction of the targeting construct into the ES cells, the cells may be plated onto a feeder layer in an appropriate medium, e.g., DMEM medium containing fetal bovine serum. The ES cell may have a single targeted locus (heterozygotic) or both loci targeted (homozygotic). Cells containing the construct may be detected by employing a selective medium and after sufficient time for colonies to grow, colonies may be picked and analyzed for the occurrence of gene targeting. As described previously, PCR may be used, with primers within and outside the construct sequence, or Southern blot analysis or PFGE, but at the target locus. Those colonies which show gene targeting may then be used for injection into mouse blastocysts. Blastocysts may be obtained from 4 to 6 week old superovulated females by flushing the uterus 3.5 days after ovulation. The ES cells may then be trypsinized and the modified cells added to a droplet containing the blastocysts. At least one, usually at least about 10, and up to about 30 of the modified embryonic stem cells may be injected into the blastocoel of the blastocyst. After injection, at least one and not more than about 15 of the blastocysts are returned to each uterine horn of pseudopregnant females. Females are then allowed to go to term and the resulting litters screened for mutant cells containing the gene-targeted deletion.

Heterozygous progeny can be readily detected by providing for a different genotype of the blastocyst and the ES cells resulting in different coat colors, chimeric progeny. A particularly useful phenotype is hair color, although any phenotype may be used or, if desired, one may look to genotype, probing for the presence of the modified genomic DNA. The pups will usually be born 16–18 days after introduction of the blastocysts into foster mothers. The heterozygous animals are screened for the presence of the targeted genomic deletion and males and females containing the deletion are mated in order to generate animals which are homozygous for the deletion.

Having now generally described the invention, the following example is provided by way of illustration and is not intended to limit the invention. All publications cited above and below are hereby incorporated in their entirety by reference.

EXPERIMENTAL

EXAMPLE 1

Deletion of 55 kb in the mouse hprt gene in ES cells by replacement-type gene targeting construct Materials and Methods Cell culture and transfection ES cell lines E14.1 and E14TG2a were kindly supplied by Dr. Rajewsky (Univ. Koln, Germany) and Dr. Hooper (Univ. Edinburgh, Scotland), respectively. ES cells were grown in antibiotic-supplemented Dulbecco's modified medium containing 15% heat-inactivated fetal bovine serum (HYCLONE), 8 µl β-mercaptoethanol and 1,000 U/ml recombinant LIF (Esgro). The cells were cultured on feeder layers of mitomycin C-treated mouse embryonic fibroblasts. E14. 1 ES cells ($2 \times 10^7/0.8$ ml) were electroporated by Gene-pulser (BioRad) in the presence of 15 µg of the targeting constructs which were excised from the plasmids, pMp4 or pMp5X by BamHI/XhoI and BamHI/SalI digestions, respectively, at 250V and 960 µF. Human hprt minigene (Reid et al., *Proc. Natl. Acad. Sci. USA*, 87:4299–4303, 1990) was transfected into ES cells by electroporation (250V, 500 IlF or 960 µF) or by lipofection (Felgner et al., *Proc. Natl. Acad. Sci. USA*, 84:7413–7417, 1987).

Cloning and mapping of genomic fragments containing the deletion junction in E14TG2a cells and construction of gene targeting constructs Analysis of genomic DNAs from E14TG2a and wild type ES cell line, digested with BamHI, identified a novel 9.2 kb BamHI containing exons 2 and 3, in E14TG2a DNA in place of the 7.0 kb fragment, present in normal mouse DNA. To clone the novel 9.2 kb fragment, a genomic library from the BamHI-digested E14.1.TG2a DNA was constructed. and clones containing the required sequences were identified by hybridization to the hprt cDNA probe. A 9.2 kb fragment, containing exon 3 sequences was cloned and a 7.0 kb BamHI-XhoI fragment containing the deletion junction sequences up to the XhoI site in exon 3, were subcloned into a bluescript (Stratagene) construct to generate a pMP4 plasmid.

To increase the length of homology present on pMP4, a 1.15 kb XhoI-EcoRI fragment containing the 3' end of exon 3 and some intron 3 sequences was cloned from normal ES cells, and inserted into its normal position of BamHI/XhoI fragment in pMP4, to generate pMP5. pMP5X was constructed by digesting pMP5 with EcoRI, generating blunted ends by using Klenow, and religating the DNA to create a unique XmnI site upstream of exon 3. The two constructs, pMP4 and pMP5X were used as the targeting constructs in the gene targeting experiments to reproduce the E14T62a deletion in E14.1 ES cells.

Selection of HPRT-targeted ES clones:

Following electroporation, $2 \times 10^6$ E14.1 ES cells were seeded onto feeder-coated 90 mn plates. After 5 to 6 days the cells were trypsinized and reseeded onto gelatin-coated 90 mm dishes at a concentration of $0.5-1 \times 10^6$ ES cells/plate. 6-thioguanine (6-TG, 5 µg/ml) was added and the medium was changed every 2 days. Seven to 10 days after the initiation of selection, 6-TG resistant ES colonies were picked up and processed for analysis.

Analysis of 6-TG resistant ES clones:

Genomic DNA extracted from 6-TG ES clones was digested with the various restriction enzymes and analyzed by Southern blot analysis using the following probes: mouse hprt cDNA obtained from ATCC;5' probe-400 bp BamHI/PstI fragment from pMP4 (See FIG. 3); and 3' probe-E2(250 bp RsaI fragment from intron 3 of the mouse hprt gene). The size of HPRT deletion in E14TG2a and in the gene targeted-ES clones was determined by PFGE using CHEF DRII (BioRad). The electrophoresis conditions were: 15 second-constant pulse interval; 200V, 20–22 C, 22 h in 0.5× TBE.

ES cell Microinjection and mouse generation:

Microinjection of ES cells into mouse blastocysts, generation and breeding of chimera mice were carried out as described (Bradley et al., *Teratocarcinomas and Embryonic Stem Cells,* Robertson, E. J. (IRL Oxford), pp. 13–151, 1987).

Results and Discussion

The first HPRT-deficient ES cell line, E14TG2a, was selected as a 6-TG spontaneous mutant of E14, an ES cell line isolated from 129 blastocysts. Previous characterization of the acquired mutation in E14TG2a identified it as a deletion that removed the first two exons of the hprt gene, its promoter and an undetermined length of upstream sequences. The deletion size was estimated to 20 kb but its precise size was not determined. In order to reproduce the E14TG2a mutation by gene targeting in E14.1 cells, the genomic fragment that contained the deletion junction from the mutant cell line was cloned, and the precise size of the deletion was determined.

Mapping analysis of E14TG2a indicated that the mutation generated a 9.2 kb BamHI fragment in place of 7.0 kb wild type fragment that spans exons 2 and 3 (See FIG. 1). A 9.2 kb fragment containing exon 3 sequences, was cloned from E14TG2a BamHI genomic library and was used to further map and size the deletion junction region (See FIG. 1). The deletion size was determined by (PFGE) using rare restriction enzymes and hybridization with the 3' and 5' probes (See FIG. 1). Hybridization of Southern blots of ScaII-digested genomic DNA isolated from E14.1 and E14TG2a with the 5' probe revealed a 170 and a 115 kb fragments, respectively (See FIGS. 3A to 3D). Hybridization of this blot with the 3' probe detected the same size 170 and 115 kb fragments, suggesting that the SaCII fragments span the entire deletion region and indicate a deletion size of 55 kb in E14TG2a. The deletion size was further confirmed by analysis of BsHII-digest DNA from both cell lines. A single 125 kb fragment was detected in E14TG2a by the 5' and 3' probes, whereas E14.1 gave rise to two fragments: 100 and 80 kb detected by 5' and 3' probes respectively. This analysis indicates the presence of a BssHII site within the deletion region and further confirms the deletion size to be 55 kb.

55 kb gene targeted-deletion of mouse HPRT gene in E14.1 cells

A 7.0 kb BanHI-XhoI fragment of the 9.2 kb deletion junction clone was subcloned into a bluescript construct to generate pMP4 targeting construct containing 6.6 kb of homology to the E14.1-hprt locus. In addition, a second targeting construct, pMP5, was constructed by adding additional 1.1 kb 3' homology (See FIG. 1). Two constructs, pPM4 and modified pMP5, containing an XmnI site in place of EcoRI located 0.25 kb upstream of exon 3 and lacking a selectable marker, were used as replacement-type targeting constructs to generate 55 kb deletion in E14.1 cells by gene-targeting. The constructs were electroplated into E14.1 cells and the cells were subjected to 6-TG selection for 7–10 days to generate 24 and 16 6-TG-resistant clones, respectively. All clones were expanded and their genomic DNA was subjected to Southern blot analysis, using the 3' probe. Gene-targeted events should result in a 9.2 kb BamHI fragment as compared to the 7.0 fragment in native E14.1 cells. Two clones, pm4.2 and pm5x.1, generated from pMP4 and pMP5.2X electroporation, respectively, gave the expected BamHI pattern (See FIGS. 5A to 5D). These 9.2 kb fragments also hybridized to the 5' probe which detected a 12 kb fragment in the parent line E14.1.

Further analysis of the above two clones (pm4.2 and pm5x.1) were carried out by BamHI-ClaI digests. Hybridization with the 3' probe revealed a 5.2 kb in pm4.2 and pm5x.1 clones, identical to that detected for E14TG2a, but missing in E14.1. The residual 9.2 kb fragment resulted from incomplete ClaI digestion most likely as a result of methylation. In contrast, hybridization with the 5' probe indicated the presence of a 4.0 BamHI-ClaI fragment in all four cell lines, as expected (See FIGS. 5A to 5D). These results indicate that pm4.2 and pm5x.1 resulted from gene targeting events.

Further confirmation of the gene-targeted 55 kb deletion was obtained from PFGE analysis (See FIG. 3A to 3D). Upon digestion with SaCII and BssHII, the clones pm4.2 and pm5x.1 gave rise to fragments identical in size to those detected for E14TG2a, indicating the reproduction of E14TG2a deletion by gene targeting in ES cells.

The inventors have demonstrated that deletions greater than 15 kb can be created by using a relatively simple replacement-type construct in the preceding example. In this example, the hprt gene was targeted with a replacement construct originated from hprt-deficient E14TG2a cells (Hooper et al., Nature, 326:292–295 1987). While others in the field have targeted the hprt gene, the deletions achieved have been on the order of 1–2 kb and 19 kb, which are significantly smaller than what the present inventors have demonstrated (Thomas et al., Cell, 51:503–512, 1987; Doetschman et al., Proc. Natl. Acad. Sci. 5:8583–8587, 1988; Zhang et al., Mol and Cell. Bio. 14:2402–2410, 1994). Using a replacement construct, the inventors have created a deletion of 55 kb in the hprt locus. These results demonstrate that replacement-type constructs can be used to delete large DNA fragments.

Although the foregoing invention has been described in some detail by way of illustration and example for purposes of clarity of understanding, it will be readily apparent to those of ordinary skill in the art in light of the teachings of this invention, that certain changes and modifications may be made thereto without departing from the spirit or scope of the appended claims.

What is claimed is:

1. A method for obtaining mammalian cells comprising a genomic deletion of 55 kb, which method comprises:

modifying the genome of mammalian cells containing a wild-type target locus by introducing a construct comprising two regions of sequences that are homologous to the 5' and 3' flanking sequences of said locus;

identifying cells comprising said 55 kb genomic deletion by selecting cells containing a selectable marker present in said construct; and recovering mammalian cells comprising said 55 kb genomic deletion.

2. The method of claim 1 wherein said target locus is the HPRT locus.

3. The method of claim 1 wherein said target locus is an MHC Class I locus.

4. The method of claim 1 wherein said target locus is an MHC Class II locus.

5. The method of claim 1 wherein said target locus is an immunoglobulin locus.

6. The method of claim 1 wherein said mammalian cells containing a wild-type target locus are selected from the group consisting of the islets of Langerhans, adrenal medulla cells, osteoblasts, osteoclasts, epithelial cells, endothelial cells, B lymphocytes, T lymphocytes, neurons, glial cells, ganglion cells, retinal cells, keratinocytes, embryonic stem (ES) cells, liver cells, bone marrow cells, and muscle cells.

7. A mammalian cell prepared by the method of claim 1.

8. A method for preparing mammalian cells deficient in the HPRT wild-type locus, which method comprises:

introducing into mammalian target cells comprising a wild-type HPRT locus a construct comprising:

a first sequence homologous to the wild-type genomic sequence immediately downstream of the second exon of the HPRT wild-type locus, wherein said first sequence is congruent with a second sequence homologous to the sequence 55 kb upstream of said first sequence in the wild-type HPRT locus to produce cells comprising a deletion in the HPRT wild-type locus;

identifying cells comprising said deletion by selecting cells containing a selectable marker present in said construct; and recovering said cells comprising said deletion, wherein said cells are deficient in the HPRT wild-type locus.

9. A mammalian cell prepared by the method of claim 8.

10. An ES cell prepared by the method of claim 8.

11. A mammalian cell line which comprises in its genome, a 55 kb deletion immediately upstream of the second intron of the HPRT locus.

12. A method for obtaining mammalian cells comprising a genomic deletion of about 55 kb, which method comprises:

modifying the genome of mammalian cells containing a wild-type target locus by introducing a construct comprising two regions of sequences that are homologous to the 5' and 3' flanking sequences of said locus;

identifying cells comprising said genomic deletion by selecting cells containing a selectable marker present in said construct; and recovering said cells comprising said genomic deletion.

13. A mammalian cell prepared by the method of claim 12.

14. An ES cell prepared by the method of claim 12.

15. The method according to claim 12, wherein said target locus is the HPRT locus.

16. The method according to claim 12, wherein said target locus is an MHC Class I locus.

17. The method according to claim 12, wherein said target locus is an MHC Class II locus.

18. The method according to claim 12, wherein said target locus is an immunoglobulin locus.

* * * * *

UNITED STATES PATENT AND TRADEMARK OFFICE
CERTIFICATE OF CORRECTION

PATENT NO.     : 5,998,209
DATED          : December 7, 1999
INVENTOR(S)    : Ava Jokobovits and Hirohisa Tsuda It is certified that error appears in the above-identified patent and that said Letters Patent is hereby corrected as shown below:

Please delete "Apr. 16, 1997" as the date the application was filed to the correct date of filing -- February 28, 1997 --.

Signed and Sealed this

Second Day of October, 2001

*Attest:*

NICHOLAS P. GODICI
*Attesting Officer*     *Acting Director of the United States Patent and Trademark Office*